United States Patent
Göttlicher et al.

(10) Patent No.: US 7,265,154 B2
(45) Date of Patent: Sep. 4, 2007

(54) VALPROIC ACID AND DERIVATIVES THEREOF AS HISTONE DEACETYLASE INHIBITORS

(75) Inventors: Martin Göttlicher, Stutensee (DE); Thorsten Heinzel, Frankfurt am Main (DE); Bernd Groner, Frankfurt am Main (DE); Peter Herrlich, Karlsruhe (DE)

(73) Assignee: Georg-Speyter-Haus Chemotherapeutisches Forschungsinstitut, Frankfurt (DE)

( * ) Notice: Subject to any disclaimer, the term of this patent is extended or adjusted under 35 U.S.C. 154(b) by 237 days.

(21) Appl. No.: 10/332,353

(22) PCT Filed: Jul. 5, 2001

(86) PCT No.: PCT/EP01/07704

§ 371 (c)(1),
(2), (4) Date: Aug. 11, 2003

(87) PCT Pub. No.: WO02/07722

PCT Pub. Date: Jan. 31, 2002

(65) Prior Publication Data
US 2004/0087652 A1    May 6, 2004

(30) Foreign Application Priority Data
Jul. 7, 2000    (EP)    ................... 00114088

(51) Int. Cl.
*A01N 37/00*    (2006.01)

(52) U.S. Cl. .................................................. 514/560
(58) Field of Classification Search ............... 514/560
See application file for complete search history.

(56) References Cited

U.S. PATENT DOCUMENTS 5,672,746 A *    9/1997    Nau et al. .................... 562/598
5,858,365 A      1/1999    Faller

FOREIGN PATENT DOCUMENTS

| WO | WO 96/06821 | 3/1996 |
| WO | WO 97/11366 | 3/1997 |
| WO | WO 97/35990 | 10/1997 |
| WO | WO 98/29114 | 7/1998 |
| WO | WO 99/23885 | 5/1999 |
| WO | WO 99/37150 | 7/1999 |
| WO | WO 02/007722 A3 | 1/2002 |

OTHER PUBLICATIONS

Wang, JF et al., *Molecular Pharmacology*, 55 (3). 521-7, (1999).

(Continued)

*Primary Examiner*—Deborah D. Carr
(74) *Attorney, Agent, or Firm*—Reed Smith, LLP

(57) ABSTRACT

The present invention relates to the use of the drug valproic acid and derivatives thereof as inhibitors of enzymes having histone deacetylase activity. The invention also relates to the use of those compounds for the manufacture of a medicament for the treatment of diseases which are associated with hypoacetylation of histones or in which induction of hyperacetylation has a beneficial effect for example by induction of differentiation and/or apoptosis in transformed cells.

11 Claims, 14 Drawing Sheets

OTHER PUBLICATIONS

Wlodarczyk BC et al., *Teratology*, 54 (6), 284-97, (1996).
Manji HK et al., *Journal of Clinical Psychiatry*, 60 Suppl 2, 27-39, (1999).
Rogiers V et al., *European Journal of Biochemistry*, 231 (2), 337-43, (1995).
Chen G et al., *Journal of Neurochemistry*, 72 (2), 879-82, (1999).
Sands SA et al., Neuropsychopharmacology, 22 (1), 27-35, (2000).
Yoshida M, *The Journal of Biological Chemistry*, vol. 265, No. 28, 17174-17179, (1990).
Fischkoff S and Walter E Jr., *Journal of Biological Response Modifiers*, 3:132-137, (1984)).
Skladchikova G et al., *NeuroToxicology*, 19 (3), 357-370, (1998).
Nordenberg J et al., *Biochemical Pharmacology*, vol. 58, pp. 1229-1236, (1999).
Tittle T and Schaumann B, *Epilepsia*, 33 (4), 729-735, (1992).
Mori H et al., Folia Pharmacologica Japonica, 74 (8), 907-23, (1978).
Nieder C et al., *Strahlentherapie und Onkologie*, vol. 176, No. 6, (Jun. 2000).
Letizia C et al., *European Journal of Internal Medicine*, 5: 325-328 (1994).
Göttlicher M et al., "Cellular Actions of Valproic Acid and Its Teratogenic Derivatives: Activation of Peroxisome Proliferator Activated Receptors (PPARs) and Differentiation of Teratocarcinoma Cells," XP-002166104, abstract.
International Search Report for PCT Patent Application No. PCT/EP01/07704, mailed May 24, 2002.
International Preliminary Examination Report for PCT Application No. PCT/EP01/07704, mailed Oct. 14, 2002.
European Search Report for European Application No. EP 00 11 4088, report completed Sep. 12, 2001.
Xu et al., "Coactivator and Corepressor Complexes in Nuclear Receptor Function," *Current Opinion in Genetics & Development*, 9, 140-147, (1999).
Warrell,, Jr. et al, "Therapeutic Targeting of Transcription in Acute Promyelocytic Leukemia by Use of an Inhibitor of Histone Deacetylase," *Accelerated Discovery*, vol. 90, No. 21, 1621-1625, (1998).
Redner et al., "Chromatin Remodeling and Leukemia: New Therapeutic Paradigms," *Blood*, vol. 94 No. 2, 417-428, (1999).
Nau et al., "Valproic Acid-Induced Neural Tube Defects in Mouse and Human: Aspects of Chirality, Alternative Drug Development, Pharmacokinetics and Possible Mechanisms," *Pharmacology & Toxicology*, vol. 69, 310-321 (1991).
Lampen et al., New Molecular Bioassays for the Estimation of the Teratogenic Potency of Valproic Acid Derivatives in Vitro: Activation of the Peroxisomal Proliferator-Activated Receptor (PPARδ), *Toxicology and Applied Pharmacology*, vol. 160, 238-249 (1999).
Chybicka et al., "The Results of Myelodysplastic Syndrome (MDS) Therapy obtained by the Polish Childrens Leukemia/Lymphoma Study Group," *Pol. Arch. Med. Wewn*, 155-158 (1998).
Werling et al., Induction of Differentiation in F9 Cells and Activation of Peroxisome Proliferator-Activated Receptor δ by Valproic Acid and its Teratogenic Derivatives, *Molecular Pharmacology*, vol. 59, 1269-1276, (2001).
Abbosh PH, Nephew KP.: "Multiple signaling pathways converge on beta-catenin in thyroid cancer", *Thyroid*. Jun. 2005;15(6):551-61. Review.
Curti BD Physical barriers to drug delivery in tumors. "*Crit. Rev. Oncol. Hematol.*" 1993, 14:29-39.
Darbinian et al: "Growth inhibition of glioblastoma cells by human Pur(alpha)". *J. Cell Physiol.* 2001189(3):334-340.
Gura T, "Systems for identifying new drugs are often faulty". *Science*, 1997, 278:1041-1042.
Hartwell LH et al "Integrating genetic approaches into the discovery of anticancer drugs". *Science* 1997, 278:1064-1068.
Jain RK. "Barriers to drug delivery in solid tumors". *Sci. Am.* 1994, 271:58-65.
Leung SK, Ohh M.: "Playing Tag with HIF: The VHL Story", *J Biomed Biotechnol.* 2002;2(3):131-135.
Lian Z, Di Cristofano A.: "Class reunion: PTEN joins the nuclear crew". *Oncogene.* Nov. 14, 2005;24(50):7394-400.
Litzow MR.: "Imatinib resistance: obstacles and opportunities". *Arch Pathol Lab Med.* May 2006;130(5):669-79.
Oliva E, Sarrio D, Brachtel EF, Sanchez-Estevez C, Soslow RA, Moreno-Bueno G, Palacios J.: "High frequency of beta-catenin mutations in borderline endometrioid tumours of the ovary", *J Pathol.* Apr. 2006; 208 (5):708-13.
Peters GJ, Backus HH, Freemantle S, van Triest B, Codacci-Pisanelli G, van der Wilt CL, Smid Km Lunec J, Calvert AH, Marsh S, McLeod HL, Bloemena E, Meijer S, Jansen G, van Groeningen CJ, Pinedo HM.: Induction of thymidylate synthase as a 5-fluorouracil resistance mechanism. *Biochim Biophys Acta.* Jul. 18, 2002;1587 (2-3):194-205.
Polakis P.: "Wnt signaling and cancer". *Genes Dev.* Aug. 1, 2000;14(15):1837-51.
Verras M, Sun Z.: "Roles and regulation of Wnt signaling and beta-catenin in prostate cancer". *Cancer Lett.* Jun. 8, 2006;237(1):22-32. Epub Jul. 14, 2005.
Zhu P, Martin E, Mengwasser J, Schlag P, Janssen KP, Gottlicher M.: "Induction of HDAC2 expression upon loss of APC in colorectal tumorigenesis". *Cancer Cell.* May 2004;5(5):455-63.

* cited by examiner

Induction of differentiation in RenCa-LacZ cells by VPA

Induction of apoptosis in MT450 breast cancer cells

| Cell Line | Organ origin | Reduction of cellular biomass at 1mM VPA |
|---|---|---|
| PC-3 | prostate | 51 % ± 3 % |
| DU-145 | prostate | 67 % ± 2 % |
| T47-D | breast, ductal | 70 % ± 2 % |
| ZR-75 | breast, ductal | 38 % ± 9 % |
| ZR-75-30 | breast, ductal | 20 % ± 2 % |
| MCF-7 | breast | 13 % ± 4 % |
| BT-549 | breast | 27 % ± 5 % |
| HT-29 | colon | 43 % ± 2 % |
| LS174T | colon | 77 % ± 4 % |
| SW-1116 | colon | 84 % ± 1 % |
| HCT-15 | colon | 26 % ± 2 % |
| COLO320DM | colon | 62 % ± 11 % |
| NCI-H23 | non-small cell lung | 38 % ± 3 % |
| NCI-H226 | non-small cell lung | 66 % ± 6 % |
| A-549 | non-small cell lung | 12 % ± 5 % |
| DMS-114 | small cell lung | 43 % ± 3 % |
| SHP-77 | small cell lung | 36 % ± 5 % |
| SK-MEL-28 | melanoma | 47 % ± 2 % |
| MALME-3M | melanoma | 105 % ± 5 % |
| OVCAR-3 | ovarian | 38 % ± 4 % |
| SK-OV-3 | ovarian | 17 % ± 7 % |
| CAPAN-1 | pancreas | 27 % ± 7 % |
| HUP-T3 | pancreas | 16 % ± 6 % |
| DETROIT-562 | head and neck | 27 % ± 3 % |
| FADU | head and neck | 29 % ± 2 % |
| A-172 | glioblastoma | 62 % ± 7 % |
| U87MG | glioblastoma | 27 % ± 9 % |
| HL-60 | leukemia | 87 % ± 2 % |
| NB-4 | leukemia | 100 % ± 1 % |
| NB-4R | leukemia | 87 % ± 1 % |

VALPROIC ACID AND DERIVATIVES THEREOF AS HISTONE DEACETYLASE INHIBITORS

This application claims priority to WO 02/007722 filed Jul. 5, 2001 and to EP 00114088.8 filed Jul. 7, 2000.

BACKGROUND OF THE INVENTION

The present invention relates to the use of the drug valproic acid and derivatives thereof as inhibitors of enzymes having histone deacetylase activity. The invention also relates to the use of those compounds for the manufacture of a medicament for the treatment of diseases which are associated with hypoacetylation of histones or in which induction of hyperacetylation has a beneficial effect for example by induction of differentiation and/or apoptosis in transformed cells.

DESCRIPTION OF THE PRIOR ART

Local remodelling of chromatin is a key step in the transcriptional activation of genes. Dynamic changes in the nucleosomal packaging of DNA must occur to allow transcriptional proteins contact with the DNA template. One of the most important mechanisms contributing to chromatin remodelling is the posttranslational modification of histones by acetylation. Change in electrostatic attraction for DNA and steric hindrance introduced by the hydrophobic acetyl group leads to destabilisation of the interaction of histones with DNA. As a result, acetylation of histones disrupts nucleosomes and allows the DNA to become accessible to the transcriptional machinery. Removal of the acetyl groups allows the histones to bind more tightly to DNA and to adjacent nucleosomes and thus maintain a transcriptionally repressed chromatin structure. Acetylation is mediated by a series of enzymes with histone acetyltransferase (HAT) activity. Conversely, acetyl groups are removed by specific histone deacetylase (HDAC) enzymes. Disruption of these mechanisms gives rise to transcriptional misregulation and may lead to leukemic transformation.

Nuclear hormone receptors are ligand-dependent transcription factors that control development and homeostasis through both positive and negative control of gene expression. Defects in these regulatory processes underlie the causes of many diseases and play an important role in the development of cancer.

Several members of the nuclear receptor superfamily have been reported to interact with basal transcription factors, including TFIIB. However, numerous lines of evidence indicate that nuclear receptors must interact with additional factors to mediate both activation and repression of target genes. A number of cofactors that associate with the ligand binding domains of estrogen (ER), retinoic acid (RAR), thyroid hormone (T3R), retinoid X (RXR), and other nuclear receptors have recently been identified. Putative coactivator proteins include SRC-1/NCoA-1, GRIP1/TIF2/NCoA-2, p/CIP/ACTR/AIB1, CBP and a variety of other factors (reviewed in Xu et al., 1999, Curr Opin Genet Dev 9, 140-147). Interestingly, SRC proteins as well as CBP have been shown to harbor intrinsic histone acetyltransferase activity and to exist in a complex with the histone acetylase P/CAF.

Many nuclear receptors, including T3R, RAR and PPAR, can interact with the corepressors N—COR and SMRT in the absence of ligand and thereby inhibit transcription. Furthermore, N—CoR has also been reported to interact with antagonist-occupied progesterone and estrogen receptors. N—COR and SMRT have been shown to exist in large protein complexes, which also contain mSin3 proteins and histone deacetylases. Thus, the ligand-induced switch of nuclear receptors from repression to activation reflects the exchange of corepressor and coactivator complexes with antagonistic enzymatic activities.

The N—CoR corepressor complex not only mediates repression by nuclear receptors, but also interacts with additional transcription factors including Mad-1, BCL-6 and ETO. Many of these proteins play key roles in disorders of cell proliferation and differentiation. T3R for example was originally identified on the basis of its homology with the viral oncogene v-erbA, which in contrast to the wildtype receptor does not bind ligand and functions as a constitutive repressor of transcription. Furthermore, mutations in RARs have been associated with a number of human cancers, particularly acute promyelocytic leukemia (APL) and hepatocellular carcinoma. In APL patients RAR fusion proteins resulting from chromosomal translocations involve either the promyelocytic leukemia protein (PML) or the promyelocytic zinc finger protein (PLZF). Although both fusion proteins can interact with components of the corepressor complex, the addition of retinoic acid dismisses the corepressor complex from PML-RAR, whereas PLZF-RAR interacts constitutively. These findings provide an explanation why PML-RAR APL patients achieve complete remission following retinoic acid treatment whereas PLZF-RAR APL patients respond very poorly. The hypothesis that corepressor-mediated aberrant repression may be causal for pathogenesis in APL is supported by the finding that trichostatin A, which inhibits histone deacetylase (HDAC) function is capable of overcoming the differentiation block in cells containing the PLZF-RAR fusion protein. Furthermore, a PML-RAR patient who had experienced multiple relapses after treatment with retinoic acid has recently been treated with the HDAC inhibitor phenylbutyrate, resulting in complete remission of the leukemia (Warrell et al., 1998, J. Natl. Cancer Inst. 90, 1621-1625).

Additional evidence that histone acetylation plays a role in cancer comes from studies on the AML1-ETO oncoprotein and on chromosomal rearrangements involving the MLL locus (Redner et al., 1999, Blood 94, 417-428).

WO 99/37150 discloses a transcription therapy for cancer comprising administering a retinoid substance and an inhibitor of histone deacetylase.

Several compounds are known to be HDAC inhibitors. Butyric acid, or butyrate, was the first HDAC inhibitor to be identified. In millimolar concentrations, butyrate is not specific for HDAC, it also inhibits phosphorylation and methylation of nucleoproteins as well as DNA methylation. Its analogue phenylbutyrate acts in a similar manner. More specific are trichostatin A (TSA) and trapoxin (TPX). TPX and TSA have emerged as potent inhibitors of histone deacetylases. TSA reversibly inhibits, whereas TPX irreversibly binds to and inactivates HDAC enzymes. Unlike butyrate, nonspecific inhibition of other enzyme systems has not yet been reported for TSA or TPX. TSA and TPX, however, exhibit considerable toxicity and are poorly bioavailable. Therefore they are of limited therapeutic use.

It is one object of the present invention to provide substances which can induce differentiation and/or apoptosis in a wide variety of transformed cells and therefore can be useful in the treatment of cancer.

The invention relies on the novel finding that valproic acid (VPA; 2-n-propylpentanoic acid) is capable of inhibiting histone deacetylases.

Valproic acid is a known drug with multiple biological activities which depend on different molecular mechanisms of action.

VPA is an antiepileptic drug.

VPA is teratogenic. When used as antiepileptic drug during pregnancy VPA can induce birth defects (neural tube closure defects and other malformations) in a few percent of born children. In mice, VPA is teratogenic in the majority of mouse embryos when properly dosed.

VPA activates a nuclear hormone receptor (PPARδ). Several additional transcription factors are also derepressed but some factors are not significantly derepressed (glucocorticoid receptor, PPARα).

VPA is hepatotoxic, which may depend on poorly metabolized esters with coenzyme A.

The use of VPA derivatives allowed to determine that the different activities are mediated by different molecular mechanisms of action. Teratogenicity and antiepileptic activity follow different modes of action because compounds could be isolated which are either preferentially teratogenic or preferentially antiepileptic (Nau et al., 1991, Pharmacol. Toxicol. 69, 310-321). Activation of PPARδ was found to be strictly correlated with teratogenicity (Lampen et al., 1999, Toxicol. Appl. Pharmacol. 160, 238-249) suggesting that, both, PPARδ activation and teratogenicity require the same molecular activity of VPA. Also, differentiation of F9 cells strictly correlated with PPARδ activation and teratogenicity as suggested by Lampen et al., 1999, and documented by the analysis of differentiation markers (Werling et al., 2001, Mol. Pharmacol. 59, 1269-1276).

It is shown in the present application, that PPARδ activation is caused by the HDAC inhibitory activity of VPA and its derivatives. Furthermore it is shown that the established HDAC inhibitor TSA activates PPARδ and induces the same type of F9 cell differentiation as VPA. From these results we conclude that not only activation of PPARδ but also induction of F9 cell differentiation and teratogenicity of VPA or VPA derivatives are most likely caused by HDAC inhibition.

The present invention is based on the finding that VPA and the derivatives described in this application are inhibitors of histone deacetylases. The finding of this novel mechanism of action of VPA and compounds derived thereof, i.e. the inhibition of enzymes with histone deacetylase activity led us to the proposition that VPA due to its HDAC-inhibitory activity should be useful to induce differentiation and/or apoptosis in a wide variety of cancer cells for two reasons: (1) these enzymes are present in all cells and (2) pilot studies with model compounds such as butyrate or TSA which are different from those described in this invention had shown that HDAC inhibitors induce differentiation in a wide variety of cells.

The activity to induce differentiation and/or apoptosis in a wide variety of transformed cells is a much more complex biological activity than only the inhibition of proliferation. In the latter case it would not be evident, why only the proliferation of transformed (tumor) but not of normal cells should be inhibited. The induction of apoptosis, differentiation or more specifically re-differentiation in dedifferentiated tumor cells provides a rationale why the compounds of this invention have beneficial effects in a wide variety of tumors by induction of differentiation and/or apoptosis. This proposition was confirmed in a wide variety of tumor cells (see examples). Antiepileptic and sedating activities follow different structure activity relationships and thus obviously depend on a primary VPA activity distinct from HDAC inhibition.

The mechanism of hepatotoxicity is poorly understood and it is unknown whether it is associated with formation of the VPA-CoA ester. The use according to the invention, e.g. HDAC inhibition, however, appears not to require CoA ester formation.

U.S. Pat. No. 5,672,746 and WO 96/06821 disclose the use of VPA and derivatives thereof for the treatment of neuredegenerative and neuroproliferative disorders.

SUMMARY OF THE INVENTION

One aspect of the present invention is the use of VPA and derivatives thereof as an inhibitor of enzymes having histone deacetylase activity. Derivatives of VPA are □-carbon branched carboxylic acids as described by formula I

wherein $R^1$ and $R^2$ independently are a linear or branched, saturated or unsaturated aliphatic $C_{2-25}$, preferably $C_{3-25}$ hydrocarbon chain which optionally comprises one or several heteroatoms and which may be substituted, $R^3$ is hydroxyl, halogen, alkoxy or an optionally alkylated amino group.

Different $R^1$ and $R^2$ residues give rise to chiral compounds. Usually one of the stereoisomers has a stronger teratogenic effect than the other one (Nau et al., 1991, Pharmacol. Toxicol. 69, 310-321) and the more teratogenic isomer more efficiently activates PPARδ (Lampen et al, 1999). Therefore, this isomer can be expected to inhibit HDACs more strongly (this invention). The present invention encompasses the racemic mixtures of the respective compounds, the less active isomers, and in particular the more active isomers.

The hydrocarbon chains $R^1$ and $R^2$ may comprise one or several heteroatoms (e.g. O, N, S) replacing carbon atoms in the hydrocarbon chain. This is due to the fact that structures very similar to that of carbon groups may be adopted by heteroatom groups when the heteroatoms have the same type of hybridization as a corresponding carbon group.

$R^1$ and $R^2$ may be substituted. Possible substituents include hydroxyl, amino, carboxylic and alkoxy groups as well as aryl and heterocyclic groups.

Preferably, $R^1$ and $R^2$ independently comprise 2 to 10, more preferably 3 to 10 or 5 to 10 carbon atoms. It is also preferred that $R^1$ and $R^2$ independently are saturated or comprise one double bond or one triple bond. In particular, one of the side chains ($R^1$) may preferably contain $sp^1$ hybridized carbon atoms in position 2 and 3 or heteroatoms which generate a similar structure. This side chain should comprise 3 carbon or heteroatoms but longer chains may also generate HDAC-inhibiting molecules. Also inclusion of aromatic rings or heteroatoms in $R^2$ is considered to generate compounds with HDAC inhibitory activity because the catalytic site of the HDAC protein apparently accommodates a wide variety of binding molecules. With the novel observation that teratogenic VPA derivatives are HDAC inhibitors, also compounds which have previously been disregarded as suitable antiepileptic agents are considered as HDAC inhibitors under this invention. In particular, but not exclusively, compounds having a propinyl residue as $R^1$ and residues of 7 or more carbons as $R^2$, are considered (Lampen et al, 1999).

Preferably, the group "$COR^3$" is a carboxylic group. Also derivatization of the carboxylic group has to be considered for generating compounds with potential HDAC inhibitory activity. Such derivatives may be halides (e.g. chlorides), esters or amides. When $R^3$ is alkoxy, the alkoxy group comprises 1 to 25, preferably 1-10 carbon atoms. When $R^3$ is a mono- or di-alkylated amino group, the alkyl substituents comprise 1 to 25, preferably 1-10 carbon atoms. An unsubstituted amino group, however, is preferred.

According to the present invention also pharmaceutically acceptable salts of a compound of formula I can be used. According to the present invention also substances can be used which are metabolized to a compound as defined in formula I in the human organism or which lead to the release of a compound as defined in formula I for example by ester hydrolysis.

In a particular embodiment, the invention concerns the use of an α-carbon branched carboxylic acid as described by formula I or of a pharmaceutically acceptable salt thereof as an inhibitor of an enzyme having histone deacetylase activity wherein $R^1$ is a linear or branched, saturated or unsaturated, aliphatic $C_{5-25}$ hydrocarbon chain, $R^2$ independently is a linear or branched, saturated or unsaturated, aliphatic $C_{2-25}$ hydrocarbon chain, but not $—CH_2—CH=CH_2$, $—CH_2—C{\equiv}CH$ or $—CH_2—CH_2—CH_3$, $R^1$ and $R^2$ are optionally substituted with hydroxyl, amino, carboxylic, alkoxy, aryl and/or heterocyclic groups, and $R^3$ is hydroxyl.

In yet another embodiment the invention concerns the use of an α-carbon branched carboxylic acid as described by formula I or of a pharmaceutically acceptable salt thereof as an inhibitor of an enzyme having histone deacetylase activity wherein $R^1$ is a linear or branched, saturated or unsaturated, aliphatic $C_{3-25}$ hydrocarbon chain, and $R^2$ independently is a linear or branched, saturated or unsaturated, aliphatic $C_{2-25}$ hydrocarbon chain, $R^1$ or $R^2$ comprise one or several heteroatoms (e.g. O, N, S) replacing carbon atoms in the hydrocarbon chain, $R^1$ and $R^2$ are optionally substituted with hydroxyl, amino, carboxylic, alkoxy, aryl and/or heterocyclic groups, and $R^3$ is hydroxyl.

In yet another embodiment of the invention $R^1$ and $R^2$ do not comprise an ester group ($—CO—O—$). The atom of $R^1$ which is next to the α-carbon of the carboxylic acid (derivative) of formula I and covalently linked to said α-carbon may be a carbon atom. The atom of $R^2$ which is next to the α-carbon of the carboxylic acid (derivative) of formula I and covalently linked to said α-carbon may be a carbon atom. $R^1$ and $R^2$ may be hydrocarbon chains comprising no heteroatoms O, N or S.

The compounds which are most preferably used according to the present invention are VPA, S-4-yn VPA, 2-EHXA (2-Ethyl-hexanoic acid).

The compounds are useful for inhibiting mammalian (for use of cell lines in in vitro assays and animal models systems) and in particular human (in vivo and in vitro) histone deacetylases HDAC 1-3 (class I) and HDAC 4-8 (class II).

The compounds may be used to induce the differentiation and/or apoptosis of cells such as undifferentiated tumour cells. Presumably, this reflects a general mechanism, as differentiation can be induced in F9 teratocarcinoma cells, MT 450 breast cancer cells, HT-29 colon carcinoma cells and several leukemia cell lines as assessed by morphological alterations and specific marker gene or protein expression. Furthermore, for example MT450 cells can be induced to undergo apoptosis (see example 6).

The invention also concerns the use of a compound of formula I for the induction of differentiation and/or apoptosis of transformed cells.

Another aspect of the present invention is the use of a compound of formula I for the manufacture of a medicament for the treatment of a disease which is associated with gene-specific hypoacetylation of histones. There are a number of diseases which are associated with aberrant repression of specific genes which correlates with a local level of histone acetylation below the regular level.

Yet another aspect of the invention is the use of a compound of formula I for the manufacture of a medicament for the treatment of a disease in which the induction of hyperacetylation of histones has a beneficial effect resulting in differentiation and/or apoptosis of a patient's tumor cells and thus causing a clinical improvement of the patient's condition. Examples of such diseases are skin cancer, estrogen receptor-dependent and independent breast cancer, ovarian cancer, prostate cancer, renal cancer, colon and colorectal cancer, pancreatic cancer, head and neck cancer, small cell and non-small cell lung carcinoma. The induction of hyperacetylation may also be beneficial by reverting inappropriate gene expression in diseases based on aberrant recruitment of histone deacetylase activity such as thyroid resistance syndrome.

The compounds and salts thereof can be formulated as pharmaceutical compositions (e.g. powders, granules, tablets, pills, capsules, injections, solutions, foams, enemas and the like) comprising at least one such compound alone or in admixture with pharmaceutically acceptable carriers, excipients and/or diluents. The pharmaceutical compositions can be formulated in accordance with a conventional method. Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. The active ingredient will preferably be administered in an appropriate amount, for example, selected from the range of about 10 mg/kg to 100 mg/kg body weight a day orally or intravenously. The dose levels are not specifically restricted as long as serum levels of 0.05 mM to 3 mM, preferably of about 0.4 mM to 1.2 mM are achieved.

Another aspect of the invention is a method for the identification of substances having histone deacetylase inhibitory activity which comprises providing a derivative of valproic acid, determining its histone deacetylase inhibitory activity, and selecting the substance if the substance has histone deacetylase inhibitory activity. Valproic acid can serve as a lead substance for the identification of other compounds exhibiting histone deacetylase inhibitory activity. Thereby compounds may be selected which show increased HDAC inhibitory activity at lower doses and serum levels and have decreased effects on the central nervous system such as sedating activity. Another parameter that may be optimised is the appearance of the hepatotoxic effect. Compounds may be selected which show a reduced liver toxicity. The derivatives may be provided by synthesising compounds which comprise additional and/or modified substituents. The HDAC inhibitory activity may be determined by a state-of-the-art technology such as transcription repression assay, a Western Blot which detects acetylation of histone H3 and/or histone H4, or by an enzymatic assay.

The transcriptional assay for repressor activity exploits activation and derepression of a Gal4-dependent reporter gene. This assay can be performed either by transient transfection of mammalian cell lines (e.g. HeLa, 293T, CV-1) or with specifically constructed permanent cell lines. Transcription factors such as thyroid hormone receptor, PPARδ, retinoic acid receptor, N—COR and AML/ETO repress transcription when they bind to a promoter containing UAS elements as fusion proteins with the heterologous DNA-binding domain of the yeast Gal4 protein. In the absence of the Gal4-fusion protein the reporter gene has a high basal transcriptional activity due to the presence of binding sites for other transcription factors in the thymidine kinase promoter. The Gal4 fusion proteins repress this activity by up to 140-fold. HDAC inhibitors induce relief of this repression which can be detected as an increase in reporter gene activity (e.g. by luciferase assay).

Histone deacetylase inhibitors induce the accumulation of N-terminally hyperacetylated histones H3 and H4. These acetylated histones can be detected by Western blot analysis of whole cell extracts or of histone preparations from histone deacetylase inhibitor-treated cells using antibodies specific for the acetylated N-terminal lysine residues of histones H3 and H4.

The enzymatic assay for HDAC activity records the release of $^3$H-labeled acetic acid from hyperacetylated substrates. Sources of HDAC activity can be co-immunoprecipitates with antibodies directed against N—CoR (or other repressors known to recruit HDACs) or crude cell extracts containing histone deacetylases (e.g. HeLa, 293T, F 9). Substrates may be either chemically $^3$H-acetylated peptides corresponding to the N-termini of histones H3 or H4 or histone proteins isolated from metabolically labelled cells which were treated with HDAC inhibitors. After extraction with ethyl acetate the release of $^3$H-labeled acetic acid is detected by liquid scintillation counting.

Yet another aspect of the invention is a method for profiling of the HDAC isoenzyme specificity of a compound as defined in formula I wherein the binding of the compound to HDAC and/or the competition for binding to HDAC is measured.

The method may comprise the following steps: HDACs are either immune precipitated with HDAC isoform specific antibodies, with antibodies directed against corepressor complexes, or with specific antibodies against recombinant HDACs overexpressed in transgenic cells. The method may further involve determination of individual HDACs present in these immune precipitates by Western blot analysis. Radiolabeled VPA or compounds according to formula I are bound to the immune precipitates. The amount of bound compound is determined through measurement of bound radioactivity after appropriate washing steps. A variation of this aspect involves binding of one labeled HDAC inhibitor such as VPA, TSA or trapoxin and competition of binding by a compound according to formula I. Another variation of the method involves the use of alternate labeling and/or detection procedures.

It is preferred that compounds are selected which specifically inhibit only a subset of HDACs.

Another aspect of the invention is the use of VPA or derivatives thereof to define genes which are induced by said compounds in cells such as primary human or rodent cells, leukemic cells, other cancer cells or tumor cell lines. Methods to define such genes that are induced by VPA include established technologies for screening large arrays of cDNAs, expressed sequence tags or so-called unigene collections. Also the use of subtractive hybridization techniques is suitable to define genes which are induced by VPA or derivatives thereof. The use of these methods to identify potential targets for drug development downstream of HDAC-inhibition, and furthermore the use of these methods to define diagnostic means in order to facilitate the therapeutic treatment of patients with suitable compounds is part of this invention. Considering the low general toxicity of VPA in the organism compared to other HDAC-inhibitors it is a specific aspect of this invention to use VPA or derivatives thereof for defining target genes which are selectively regulated or not regulated by VPA, particularly also in comparison to other HDAC inhibitors like trichostatin A.

The present invention also concerns a diagnostic method to identify tumors comprising the step of testing whether a tumor is responsive to treatment with compounds as defined by formula I. The method preferably comprises the method for the identification of genes induced by VPA or a derivative thereof described supra. In a particular embodiment, the diagnostic method comprises the use of nucleic acid technology, preferably of hybridization or polymerase chain reaction for detection. Other types of nucleic acid technology, however, may be employed. In another embodiment the method comprises the use of specific antibodies against differentially regulated proteins for detection. For this purpose proteins encoded by the genes showing deregulation of their expression upon VPA treatment would be expressed e.g. in recombinant expression systems and antibodies directed against these proteins would be generated. Subsequently such antibodies could be used (or patterns of antibodies) to characterize the status of a tumor or tumor cells for diagnostic and/or prognostic reasons.

The present invention provides novel possibilities to treat various cancer diseases. Applicant found that VPA and derivatives thereof are potent HDAC inhibitors. The HDAC inhibitors known so far are either nonspecific like butyrate, or toxic or poorly bioavailable in the whole organism like TSA and TPX. VPA has the advantage that it is already an approved drug and has been used over decades for the treatment of epilepsy in human. Thus, a vast amount of data concerning pharmaceutical acceptability and the lack of serious side effects are available. Thus VPA should be a suitable drug for the use in humans to induce differentiation and/or apoptosis in transformed cells and by that to exert beneficial effects in a wide variety of patients suffering from cancer.

or SKOV3 ovarian carcinoma cells, SKBR3, MCF7, MDA-MB453 and MDA-MB468 breast carcinoma cells, and A431 squamous cell carcinoma cells (B) were incubated with the indicated concentrations of valproic acid (VPA). The relative number of viable cells was determined using the enzymatic MTT assay, measuring cellular metabolic activity, as described in Example 7. Each point represents the mean of a set of data determined in triplicate (example 7).

Figure 8:
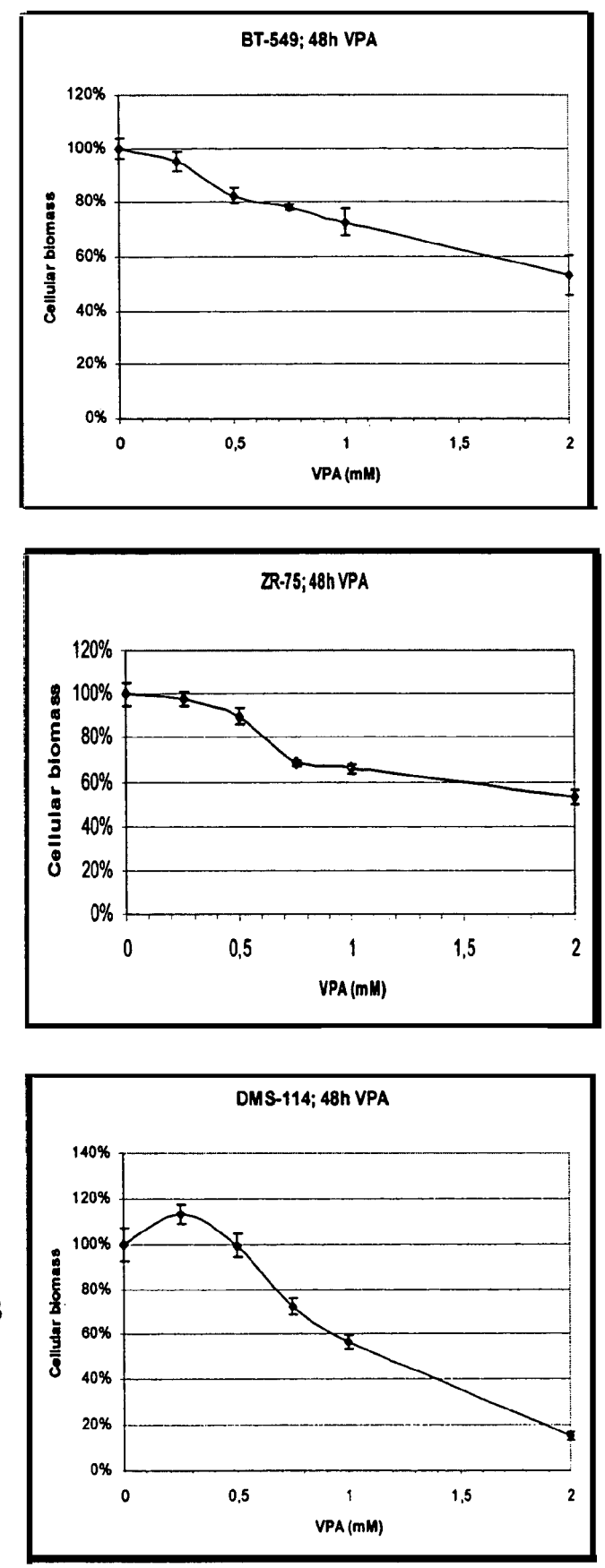
Figure 8:
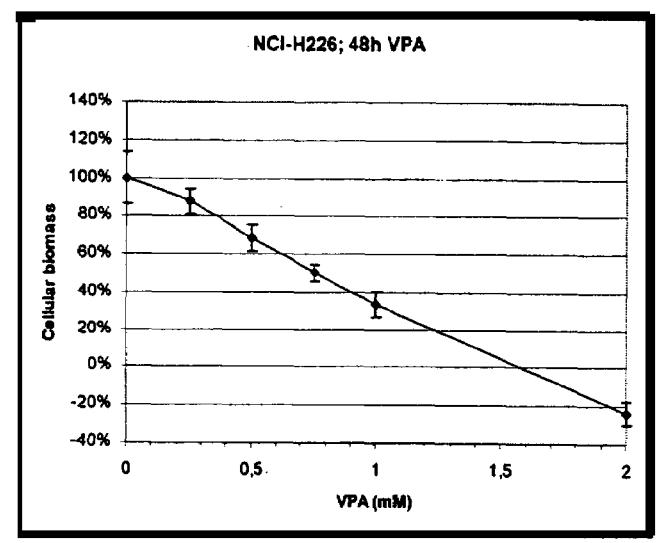
Figure 8:
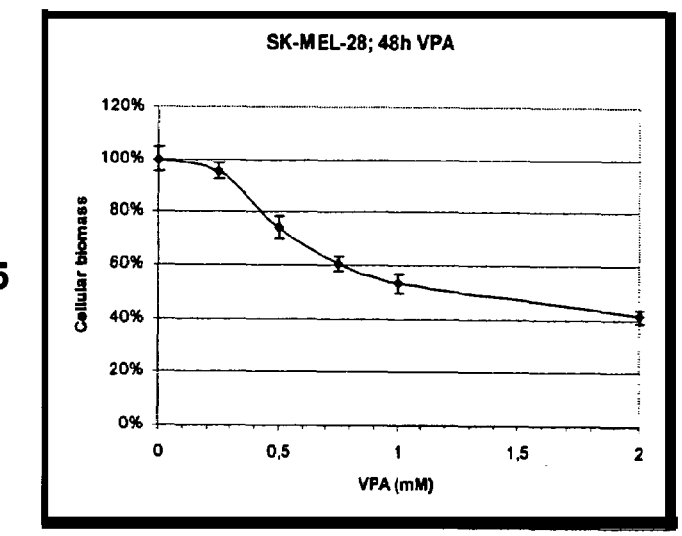
Figure 8:
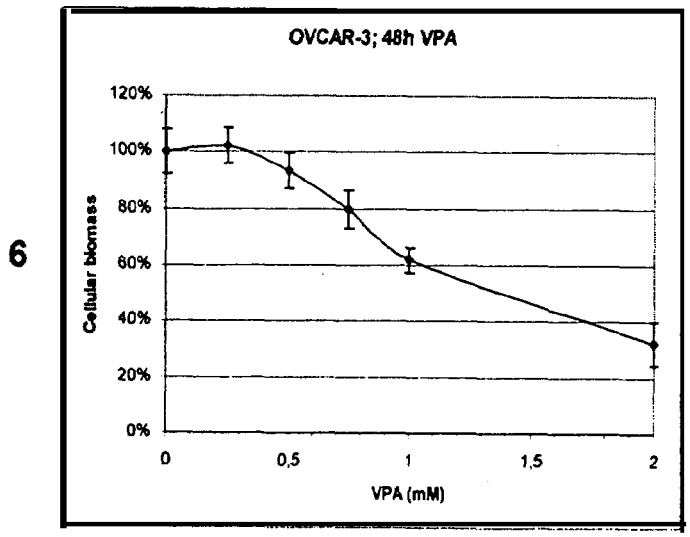
Figure 8:
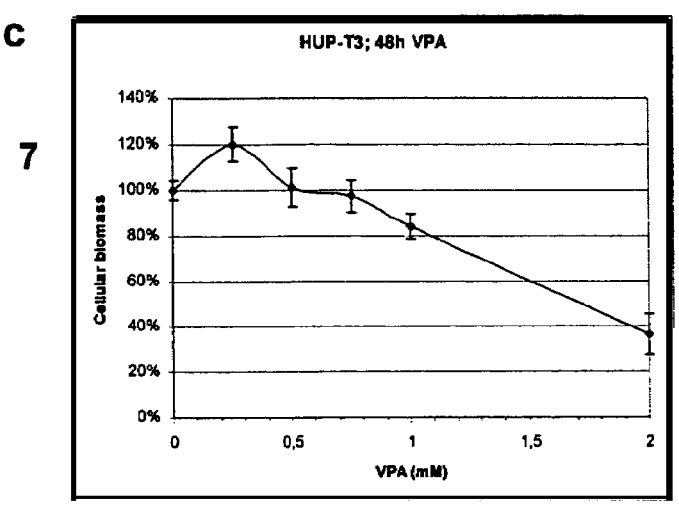
Figure 8:
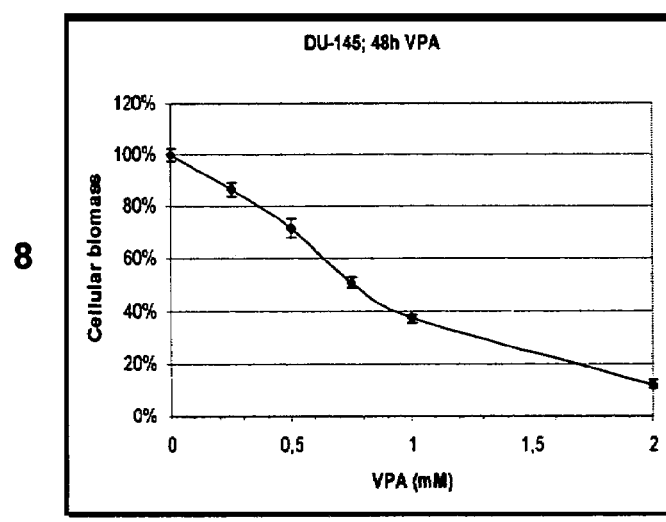
Figure 8:
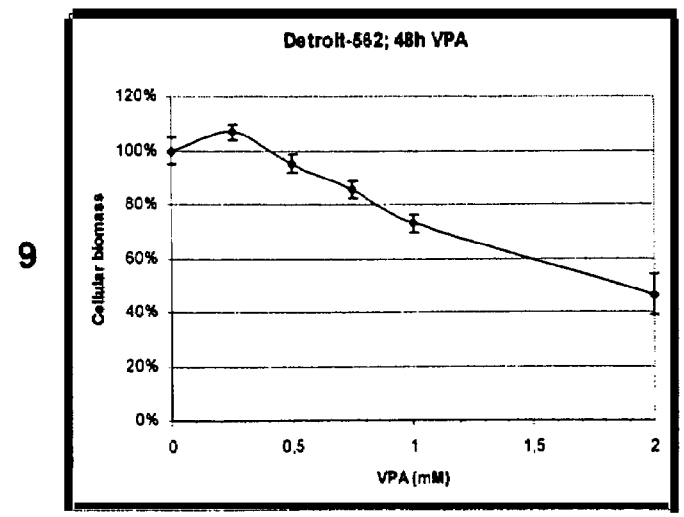
Figure 8:
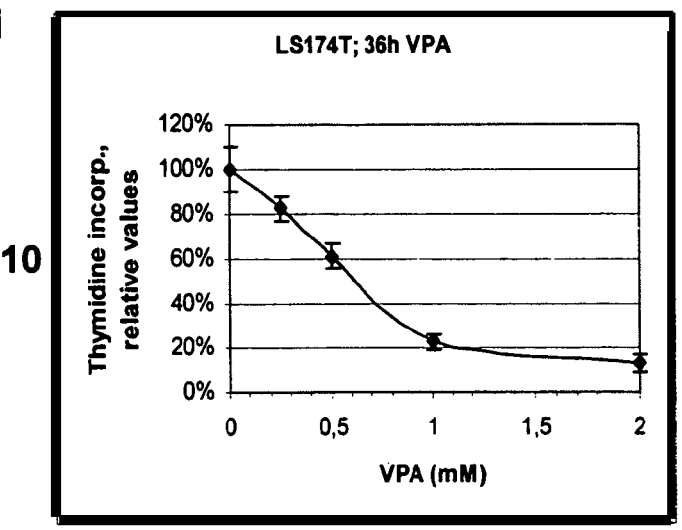
Figure 8:
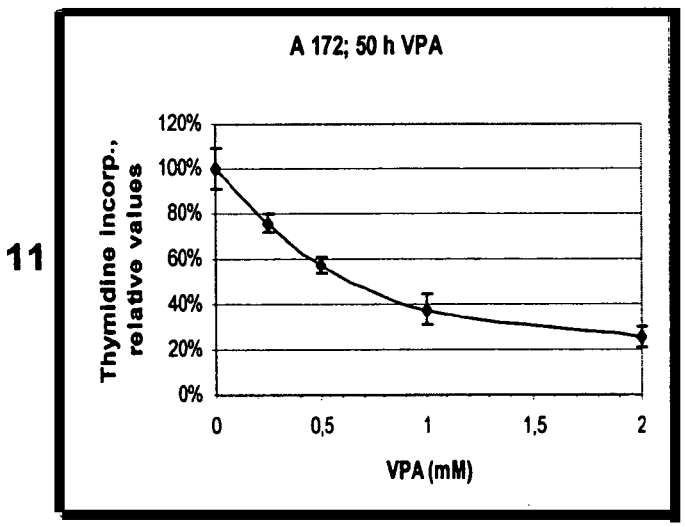
Figure 8:
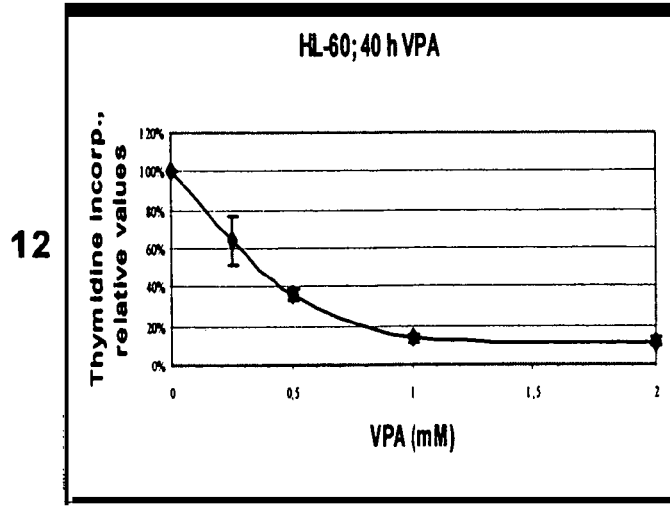

FIG. 8 shows the reduction in cellular biomass after treatment of cell cultures with VPA (example 8)

DETAILED DESCRIPTIONS OF PREFERRED EMBODIMENTS

The following examples further illustrate the invention.

EXAMPLE 1

Activation of a PPARδ-Glucocorticoid Receptor Hybrid Protein by VPA

Figure 1:
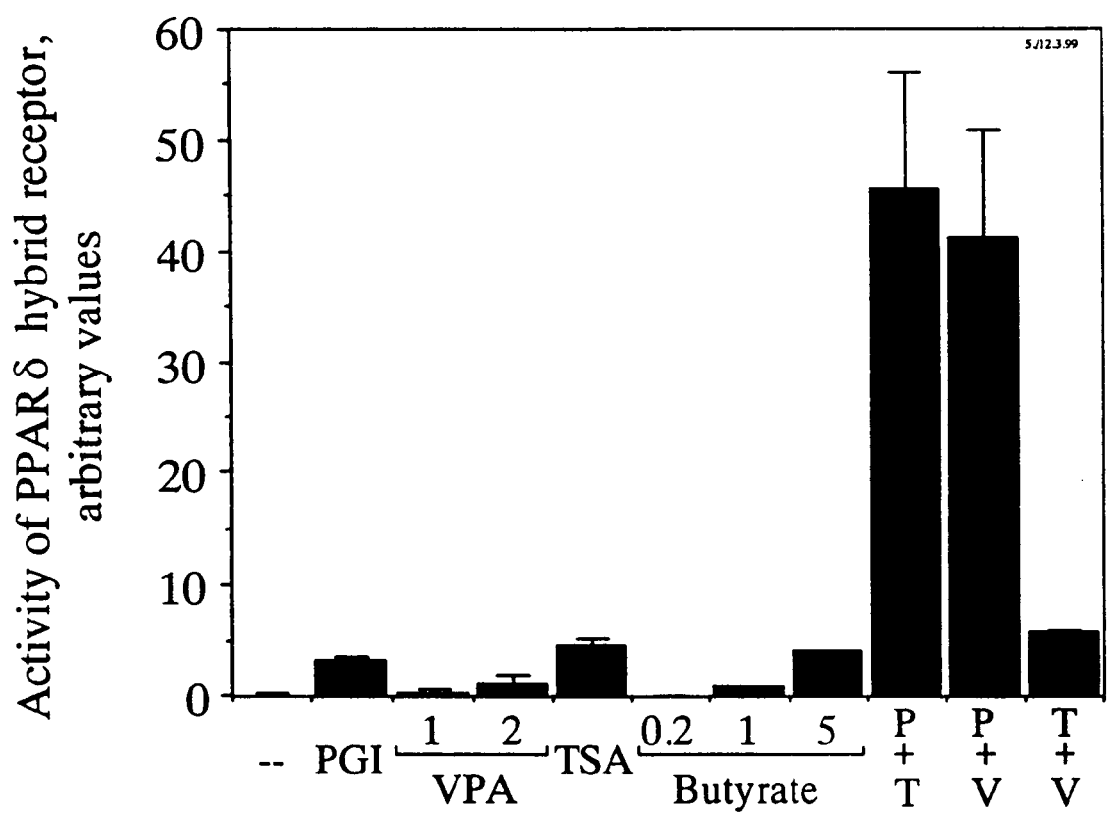
FIG. 1 describes the histone deacetylase inhibitor-like activation of PPARδ by VPA (example 1).

A reporter gene cell line for activation of the PPARδ ligand binding domain was constructed in CHO cells. A subclone of CHO cells was used which contained a transgenic reporter gene expressing a secreted form of the human placental alkaline phosphatase under control of the glucocorticoid receptor-dependent LTR-promoter of the mouse mammary tumor virus (Göttlicher et al. (1992) Proc. Natl. Acad. Sci. USA 89, pp. 4653-4657). A hybrid receptor comprising the amino-terminus of the glucocorticoid receptor fused to the ligand binding domain of PPARδ was expressed in these cells essentially as described for the expression of the corresponding hybrid of PPARα (Göttlicher et al., 1992, ibd.). The ligand binding domain of PPARδ was used starting at amino acid 138 as deduced from the sequence published by Amri et al. (J. Biol. Chem. 270 (1995) pp. 2367-2371). Activation of the PPARδ ligand binding domain in these cells induces expression of the alkaline phosphatase reporter gene which is detectable by an enzymatic assay from the cell culture supernatant. Similar cells expressing the full length glucocorticoid receptor served as negative controls for specificity of receptor activation. For the experiment shown in FIG. 1 the PPARδ hyrid receptor expressing cells were seeded at 20% confluency into 24-well culture dishes and treated for 40 h with the PPARδ ligand carbocyclic prostaglandin $I_2$ (PGI, 5 µM), VPA (1 or 2 mM), or the histone deacetylase inhibitors sodium butyrate (0,2-5 mM) and trichostatin A (TSA, 300 nM). Reporter gene activity was monitored by an enzymatic assay (alkaline phosphatase). Values except for butyrate are means±S.D. from triplicate determinations in 2 independent experiments which were normalized according to cPGI-induced activity (FIG. 1). The highly synergistic activation of the reporter gene by VPA together with the PPARδ ligand cPGI (P+V) which is similar to the synergistic activation by Trichostatin A together with cPGI (P+T), and the lack of synergism with trichostatin (T+V) or butyrate (not shown) indicate that VPA does not act like a bona fide ligand to PPARδ. VPA rather affects PPARδ activity by a mechanism which lies in the same sequence of events by which also the inhibitors of corepressor-associated histone deacetylases induce transcriptional activity of PPARδ.

EXAMPLE 2

Activation of Transcriptional Repressors by VPA

Figure 2:
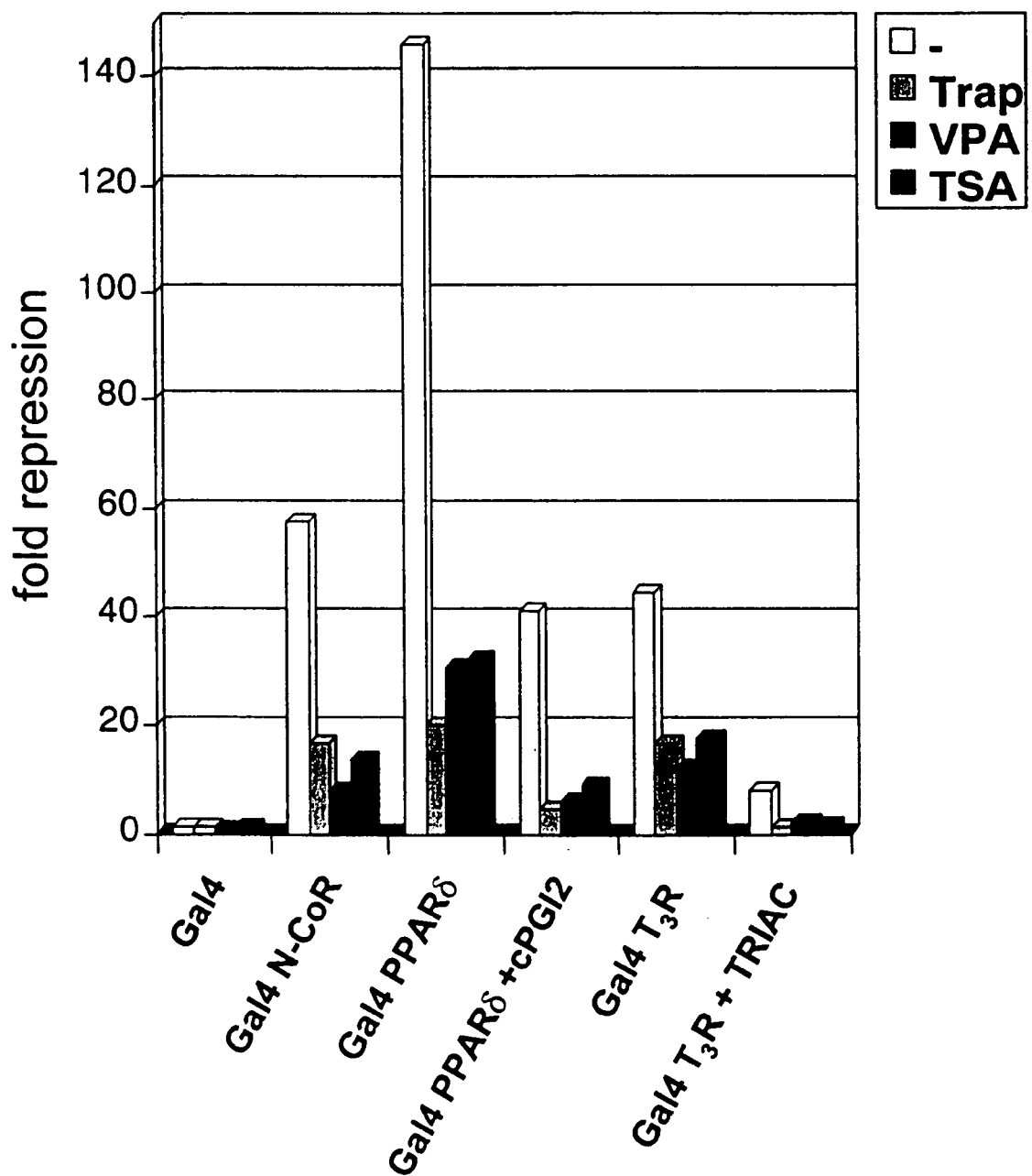
FIG. 2 shows that VPA activates several transcription factors in addition to PPARδ (example 2).

The transcription factors thyroid hormone receptor (TR), peroxisome proliferator activated receptor □ (PPARδ), retinoic acid receptor (RAR), the corepressor N—CoR and the AML/ETO fusion protein repress transcription when they bind to a promoter containing UAS sites (Gal4 response element) as fusion proteins with the heterologous DNA binding domain of the yeast Gal4 protein. In the absence of the Gal4 fusion protein a luciferase reporter gene is transcribed at a high basal level due to the presence of binding sites for other transcription factors in the thymidine kinase (TK) promoter. Hela cells were transfected with a UAS TK luciferase reporter is plasmid (Heinzel et al., 1997, Nature 387, pp 43-48) and expression plasmids for the indicated Gal4 fusion proteins using the calcium phosphate precipitate method. After 24 h the medium was changed and cells were incubated with histone deacetylase inhibitors for a further 24 h. Transcriptional repression is measured as luciferase activity relative to the baseline of cells transfected with an expression plasmid for the Gal4 DNA binding domain alone (FIG. 2). The Gal4 fusion proteins repress this baseline activity by up to 140 fold. VPA at a concentration of 1 mM (close to the serum levels which are reached during therapeutic use) induces relief of this repression which is indicated as an increase in reporter gene activity. A relief of repression is also found after treatment with established histone deacetylase inhibitors (10 nM Trapoxin, 100 nM TSA) as well as after partial activation of TR and PPARδ by their respective ligands. A combination of ligand and HDAC inhibitors (including VPA) results in a synergistic effect, indicating that different molecular mechanisms are involved. FIG. 2 shows that VPA affects the activity of several distinct transcription factors and cofactors. This finding suggests that VPA acts on a common factor in the regulation of gene expression such as corepressor-associated histone deacetylases rather than on individual transcription factors or receptors (e.g. as a ligand).

EXAMPLE 3

Accumulation of Hyperacetylated Histones in VPA-Treated Cells

Figure 3:
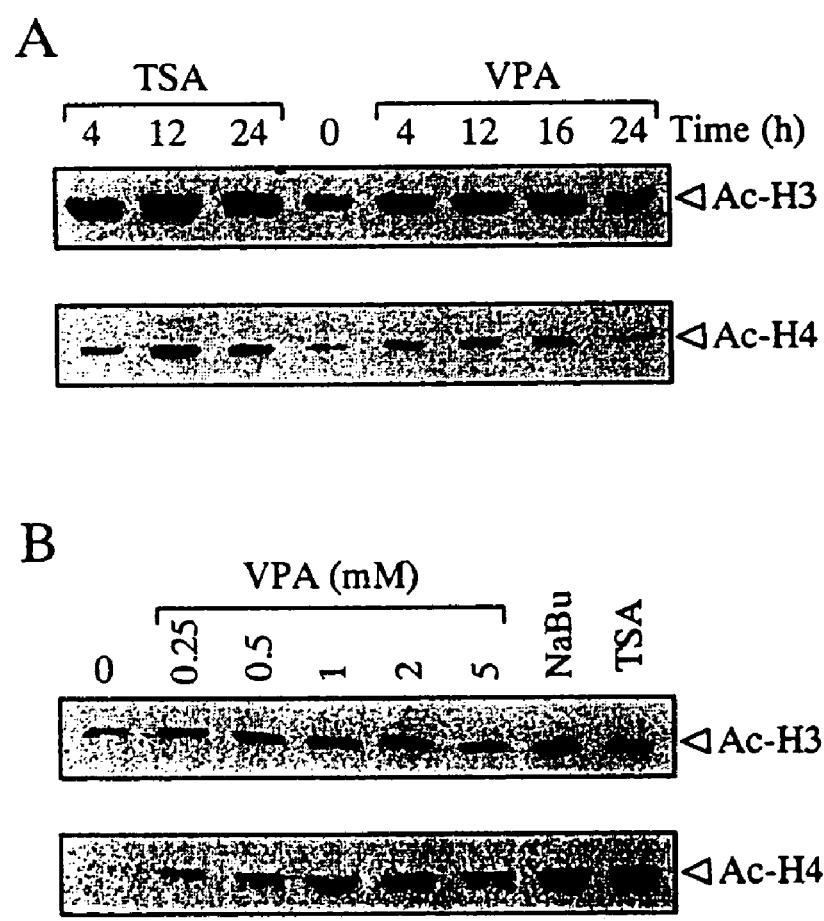
FIG. 3 shows VPA-induced accumulation of hyperacetylated histones H3 and H4 (example 3).

VPA and established histone deacetylase inhibitors like sodium butyrate (NaBu) or trichostatin A (TSA) induce the accumulation of hyperacetylated histones H3 and H4. These acetylated histones can be detected by Western blot analysis in cell extracts of appropriately treated cells. FIG. 3 shows the results of such an analysis from a representative experiment. In this experiment both the time course of VPA-induced hyperacetylation (A) and the required VPA concentration (B) were determined.

(A) For the time course analysis F9 cells were seeded into 6-well culture dishes 30 h before the intended time point of analysis. Individual cultures were treated at the indicated time points before analysis by addition of 10-fold concentrated stock solutions in culture medium of VPA or trichostatin A. Whole cell extracts were prepared by rinsing the cell cultures twice in ice-cold phosphate buffered saline and lysis of cells in 250 µl of sample buffer for denaturing SDS gel electrophoresis. DNA of collected samples was sheared by sonication and samples were separated on a 15% denaturing polyacrylamide gel. Acetylated histones H3 and histone H4 were detected by Western blot analysis using commercially available antibodies (Upstate Biotechnology) specific for the acetylated forms of histones (Ac-H3, Cat-Nr.: 06-599; Ac-H4, Cat-Nr.: 06-598). Equal loading of the lanes was confirmed by staining a part of the polyacrylamide gel by Coomassie blue.

(B) For determination of the required VPA dose F9 cells were cultured in 6-well culture dishes for 8 h prior to addition of VPA at the indicated concentrations. Whole cell extracts were prepared 16 h after treatment as described above. Analysis for acetylated histones H3 and H4 was performed as described in (A). VPA concentrations in the range of blood serum levels reached during therapeutic use of VPA as antiepileptic agent in humans induce hyperacytlation of histones H3 and H4. At serum levels only slightly exceeding those intended for antiepileptic therapy VPA induces histone hyperacetylation as efficiently as sodium butyrate or trichostatin A used at concentrations which are expected to have a maximum effect. This experiment indicates that VPA or a metabolite formed in F9 cells inhibits histone deacetylase activity.

EXAMPLE 4

VPA and Derivatives Inhibit Histone Deacetylase Activity in Vitro

Figure 4:
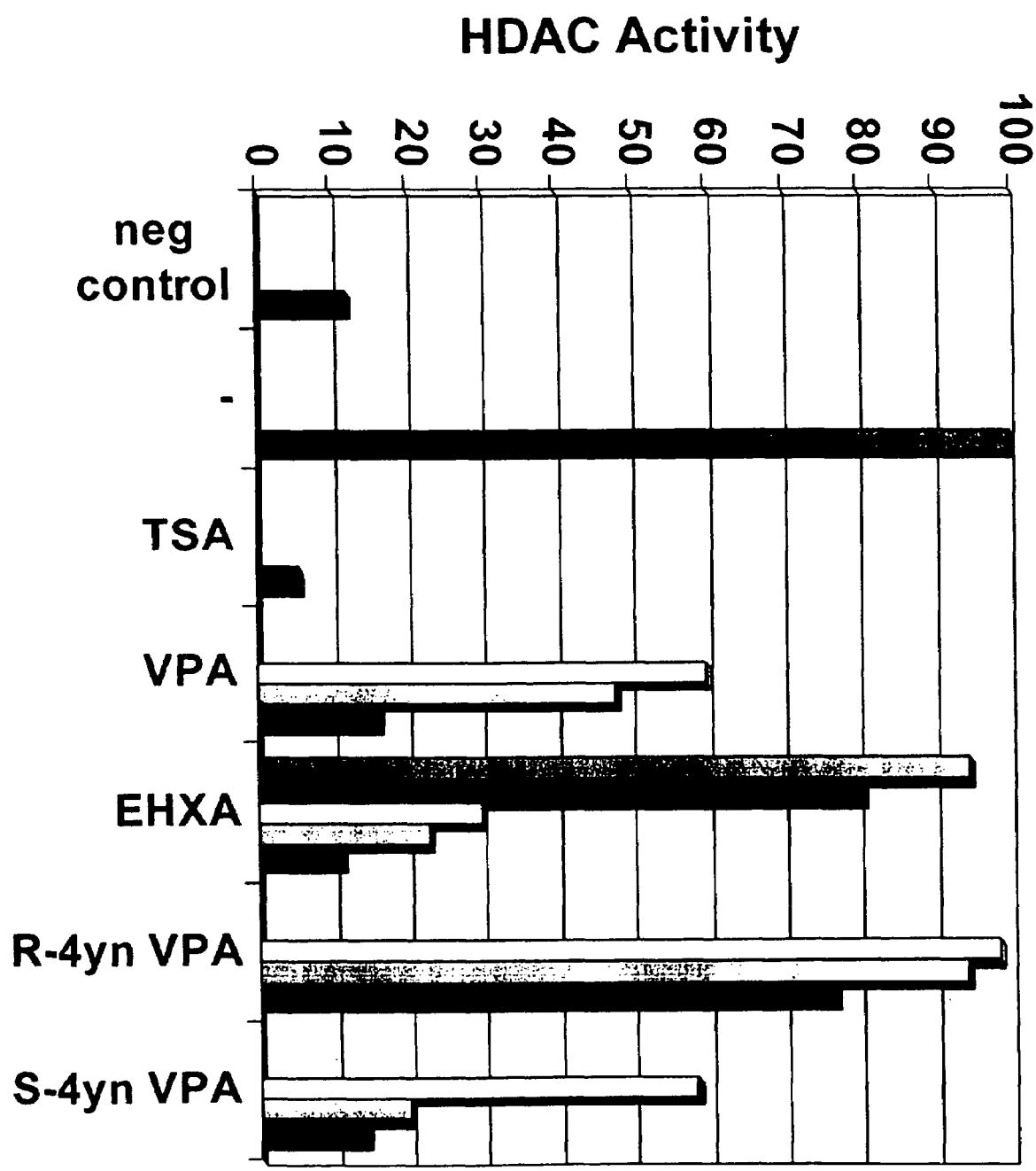
FIG. 4 shows the biochemical analysis of histone deacetylase activity in the absence or presence of VPA (example 4).

Immune precipitates from whole cell extracts using antibodies against the corepressor N—COR or mSin3 contain histone deacetylase activity. This enzymatic activity is measured by incubating the immune precipitates with radioactively acetylated histone substrates from cells in which histones have been hyperacetylated in the presence of $^3$H-acetate. The release of $^3$H-acetate is detected as a measure of enzymatic activity by extraction with ethyl acetate and subsequent liquid scintillation counting (FIG. 4). Addition of the histone deacetylase inhibitor trichostatin A (TSA, $10^{-7}$ M) to the reaction in vitro severely inhibits the enzymatic activity. VPA (from left to right 0.2 mM, 1 mM, 5 mM) and the related compounds ethyl hexanoic acid (EHXA, from left to right 0.008 mM, 0.04 mM, 0.2 mM, 1 mM, 5 mM), R-4-yn VPA (from left to right 0.2 mM, 1 mM, 5 mM) and S-4-yn VPA (from left to right 0.2 mM, 1 mM, 5 mM) were tested for HDAC inhibitory activity. The assays were performed with N—CoR immunoprecipitates from 293T cells in duplicate. Immunoprecipitates were pretreated with HDAC inhibitors for 15 min prior to the addition of substrate and subsequent incubation for 2.5 h at 37° C. (untreated enzyme activity 2,205 cpm=100%). Precipitates of a preimmune serum served as a negative control. $EC_{50}$ values are 0.6 mM for VPA, 0.2 mM for EHXA and 0.3 mM for S-4-yn VPA, whereas the stereoisomer R-4-yn VPA is inactive. These data show that VPA by itself rather than a cellular metabolite inhibits histone deacetylase activity.

EXAMPLE 5

Induction of Cell Differentiation in F9 Teratocarcinoma, HT-29 Colonic Cancer, and RenCa Renal Carcinoma Cells.

Figure 5A:
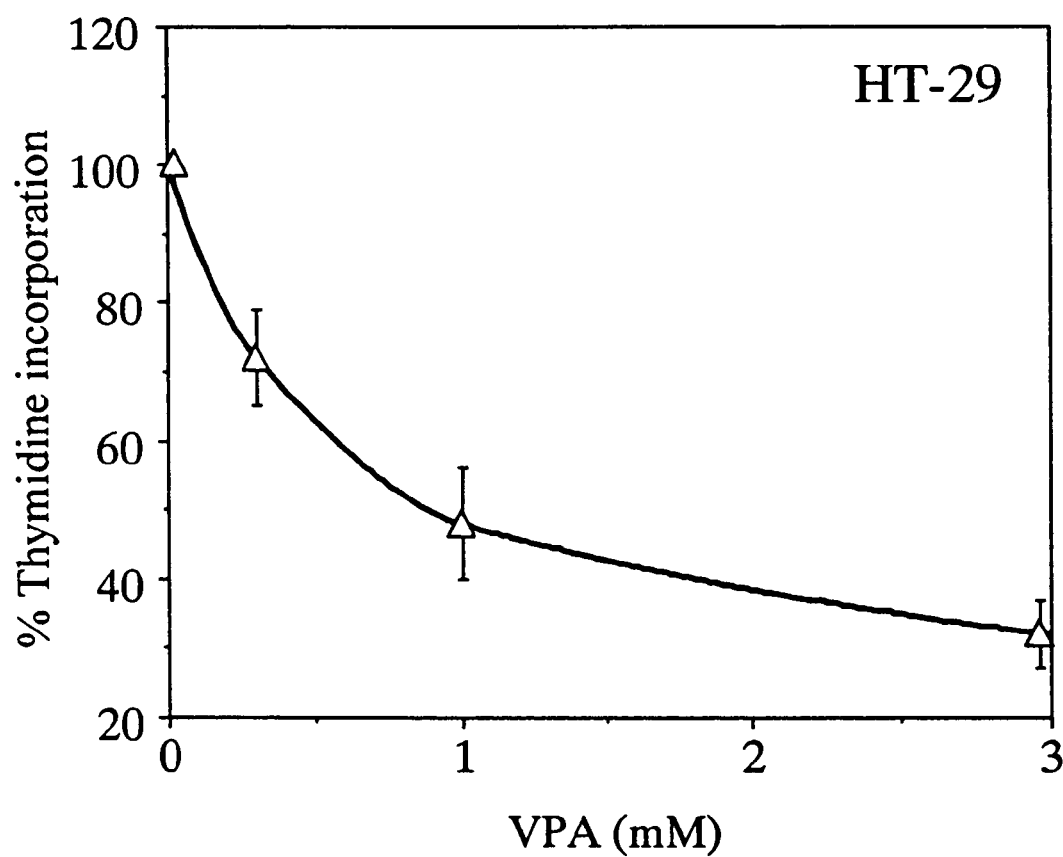
FIG. 5 shows indicators of VPA induced differentiation in HT-29 colonic carcinoma cells, F9-teratocarcinoma cells, and RenCa renal carcinoma cells. The phenotypes of F9-teratocarcinoma cells differentiated by VPA or the histone deacetylase inhibitor trichostatin A appear identical (example 5).
Figure 5B:
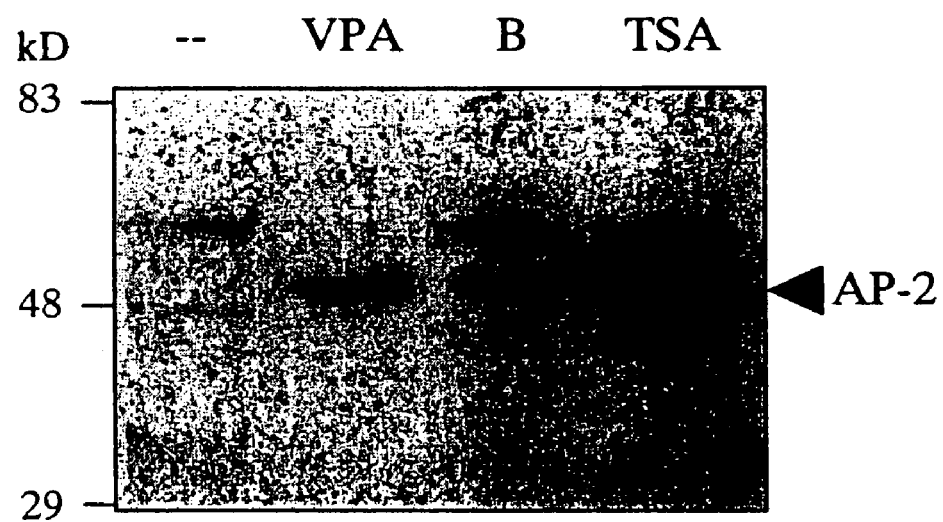

Histone deacetylase inhibitors and VPA in particular induce differentiation of dedifferentiated tumorigenic cells. Cell differentiation is associated with cell cycle arrest, morphological alterations and the appearance of expression of markers of the differentiated phenotype. Morphological alterations where determined by microscopic evaluation of F9 and HT-29 cells. One parameter of differentiation, the cell cycle arrest, was shown in F9 teratocacrcinoma, estrogen independent MT-450 breast cancer and HT-29 colonic carcinoma cells by means of the reduced incorporation of $^3$H-thymidine into cultured cells. F9 and HT-29 cells were cultured for 36 h in the absence or the presence of 1 mM VPA in 96-well culture dishes. 37 kBq of $^3$H-thymidine were added for additional 12 h of culture. MT-450 cells were cultured for 72 h prior to a 1 h $^3$H-thymidine labelling period. Incorporation of $^3$H-thymidine into DNA was determined by automatic cell harvesting and liquid scintillation counting. VPA pretreatment reduced the rate of thymidine incorporation by 48±5%, 63±8%, and 52±8% in F9, MT-450, and HT-29 cells, respectively. The dose-response for the reduction of thymidine incorporation into HT-29 cells (FIG. 5A) was determined by the same experimental procedure. In addition, the induction of a cell differentiation marker was shown in F9 teratocarcinoma cells (FIG. 5B).

F9 teratocarcinoma cells were treated for 48 h with VPA (1 mM), sodium butyrate (B, 1 mM) and trichostation A (TSA, 30 nM). Differentiation was followed by morphological criteria, a reduced rate in the increase of cell number (e.g. cell cycle arrest, data not shown), the drop of $^3$H-thymidine incorporation by 48% during a 12 h pulse labeling period (see above) and the appearance of nuclear AP-2 protein (FIG. 5B) as a specific marker of histone deacetylase inhibitor-induced differentiation of F9 cells. Nuclear AP-2 protein was detected in nuclear extract which had been prepared by mild detergent lysis (25 mM Tris, pH 7.5; 1 mM EDTA, 0.05% NP40) of treated or non-treated F9 cells, recovery of nuclei by centrifugation (3000×g, 5 min) and lysis of nuclei in sample buffer for denaturing SDS gel electrophoresis. Nuclear extracts were separated on a 9% SDS polyacrylamide gel. AP-2 protein was detected by Western blot analysis using a rabbit polyclonal antibody (Santa Cruz, Cat.-No.: SC-184) at a dilution of 1/1000 in Tris buffered saline containing 3% non-fat dry milk and 0.05% Tween 20. Both VPA and trichostatin A induce nuclear AP-2 protein whereas the activity of butyrate at the chosen concentration is weak. Since appearance of AP-2 is a delayed effect which is only detectable after 36 to 40 h of VPA treatment the weak activity of butyrate may be caused by efficient metabolism of the compound. Nevertheless, VPA induces differentiation of the epithelial F9 cell line in a way indistinguishable from differentiation by other histone deacetylase inhibitors.

Figure 5C:
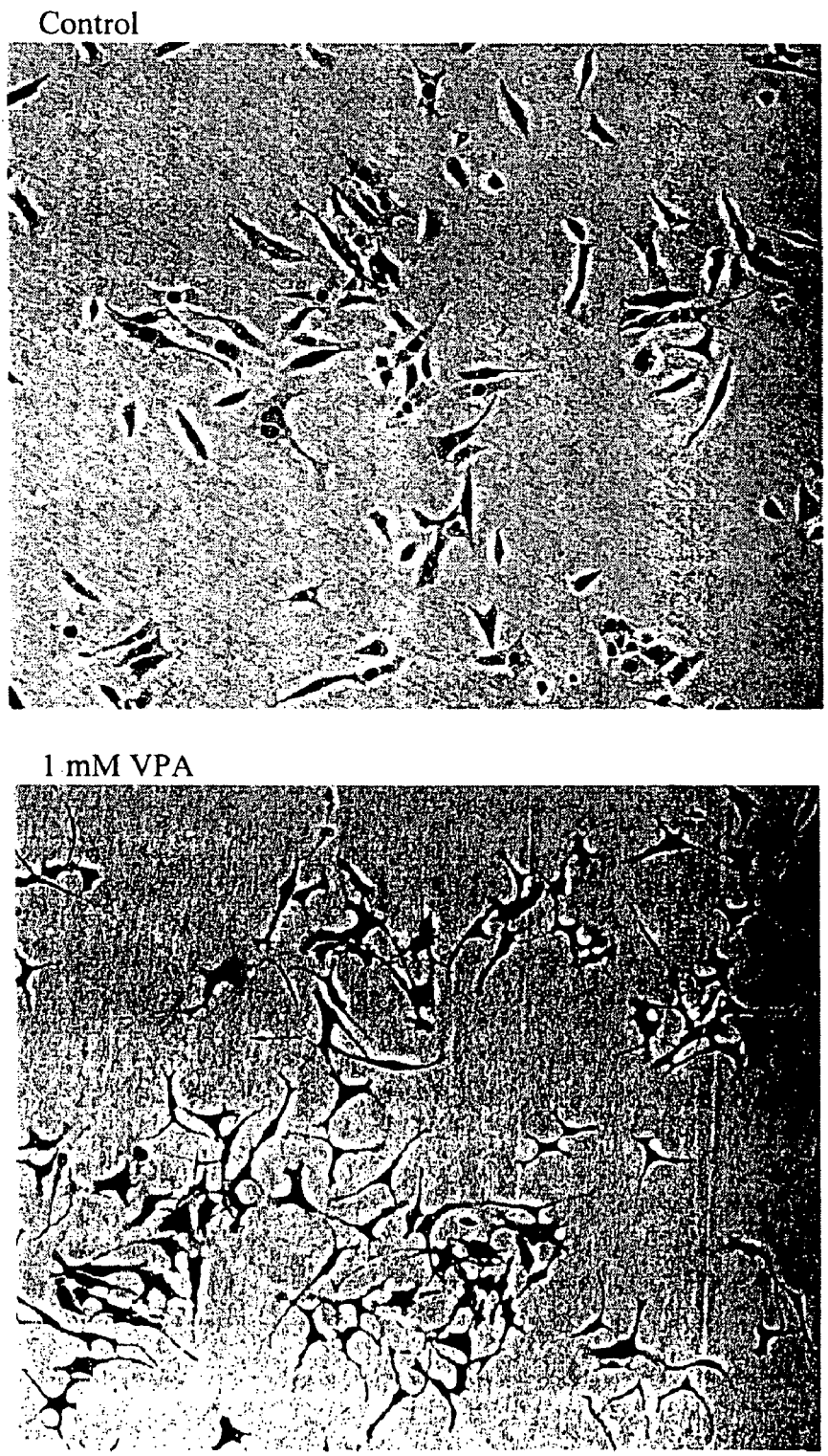

Induction of differentiation in RenCa-LacZ cells by VPA was determined by alterations in cell morphology. RenCa-LacZ cells were cultured for 36 h either in the absence or the presence of 1 mM VPA. Morphological alterations were observed by phase contrast microscopy and micrographs of representative fields were taken (FIG. 5C)

EXAMPLE 6

Induction of Apoptosis in MT-450 Breast Cancer Cells

Figure 6:
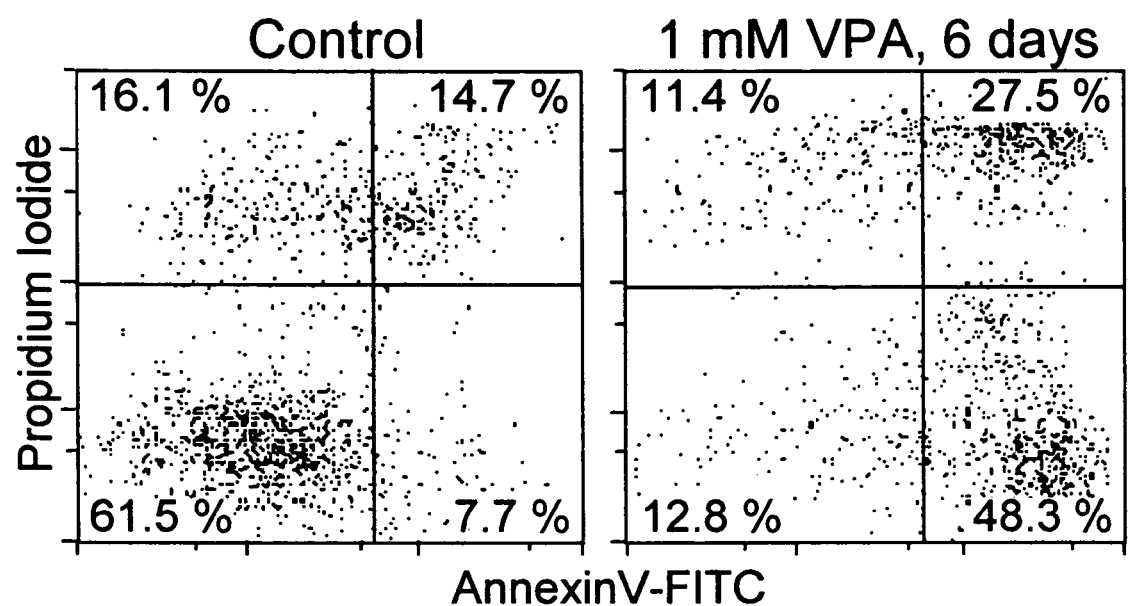
FIG. 6 shows induction of apoptosis in MT450 breast cancer cells (example 6).

MT-450 cells were cultured for 72 h in the absence or presence of 1 mM VPA. Apoptotic cells were detected by flow cytometric analysis after staining of cell surface exposed phosphatidylserine with FITC-conjugated annexin V (Becton Dickinson) according to supplier's instructions. Dead cells were excluded by propidium iodide staining. Cells positive for annexin V and negative for propidium iodide uptake (lower right quadrant in FIG. 6) were judged and counted as apoptotic cells.

EXAMPLE 7

Loss of Viable Tumor Cells Upon Treatment with Valproic Acid (MTT Tests)

Cell Lines and Cell Culture

Human MDA-MB468, MDA-MB453 and SKBR3 breast carcinoma cells, A431 squamous cell carcinoma cells, and SKOV3 ovarian carcinoma cells were maintained in Dulbecco's modified Eagle's medium (DMEM, BioWhittaker, Verviers, Belgium) supplemented with 10% heat inactivated fetal bovine serum (FBS), 2 mM L-glutamine, 100 units/ml penicillin, and 100 µg/ml streptomycin. Human MCF7 breast carcinoma cells were grown in RPMI medium supplemented as described above.

Renal cell carcinoma (Renca) cells stably transfected with plasmid pZeoSV2/lacZ encoding E. coli β-galactosidase (Renca-lacZ cells) (Maurer-Gebhard et al., Cancer Res. 58: 2661-2666, 1998) were grown in RPMI-1640 medium supplemented with 8% FBS, 2 mM L-glutamine, 100 U/ml penicillin, 100 µg/ml streptomycin, 0.25 mg/ml Zeocin. Renca-lacZ cells cotransfected with plasmids pSV2ErbB2N and pSV2neo encoding c-erbB2 and neomycin resistance (Renca-lacZ/ErbB2) (Maurer-Gebhard et al., Cancer Res. 58: 2661-2666, 1998), or plasmids pLTR-EGFR or pLTR-EGFRvIII and pSV2neo encoding epidermal growth factor (EGF) receptor, the oncogenically activated EGF receptor variant EGFRvIII, and neomycin resistance (Renca-lacZ/EGFR and Renca-lacZ/EGFRvIII) (Schmidt et al., Oncogene 18: 1711-1721, 1999) were grown in the same medium further containing 0.48 mg/ml G418.

Cell Viability Assays

Tumor cells were seeded in 96 well plates at a density of $1 \times 10^4$ cells/well in normal growth medium. Valproic acid was added at final concentrations of 1 or 3 mM to triplicate samples and the cells were incubated for 40 h (Renca-lacZ, Renca-lacZ/ErbB2, Renca-lacZ/EGFR, Renca-lacZ/EGFRvIII, SKBR3 and SKOV3 cells) or 70 h (A431, MCF7, MDA-MB453 and MDA-MB468 cells). Control cells were grown in the absence of valproic acid. Ten µl of 10 mg/ml 3-(4,5-dimethylthiazole-2-yl)-2,5 diphenyltetrazolium bromide (MTT) (Sigma, Deisenhofen, Germany) in PBS were added to each well and the cells were incubated for another 3 h. Cells were lysed by the addition of 90 µl of lysis buffer (20% SDS in 50% dimethyl formamide, pH 4.7). After solubilization of the formazan product, the absorption at 590 nm was determined in a microplate reader (Dynatech, Denkendorf, Germany) and the relative amount of viable cells in comparison to cells grown without the addition of valproic acid was calculated.

Results

Figure 7:
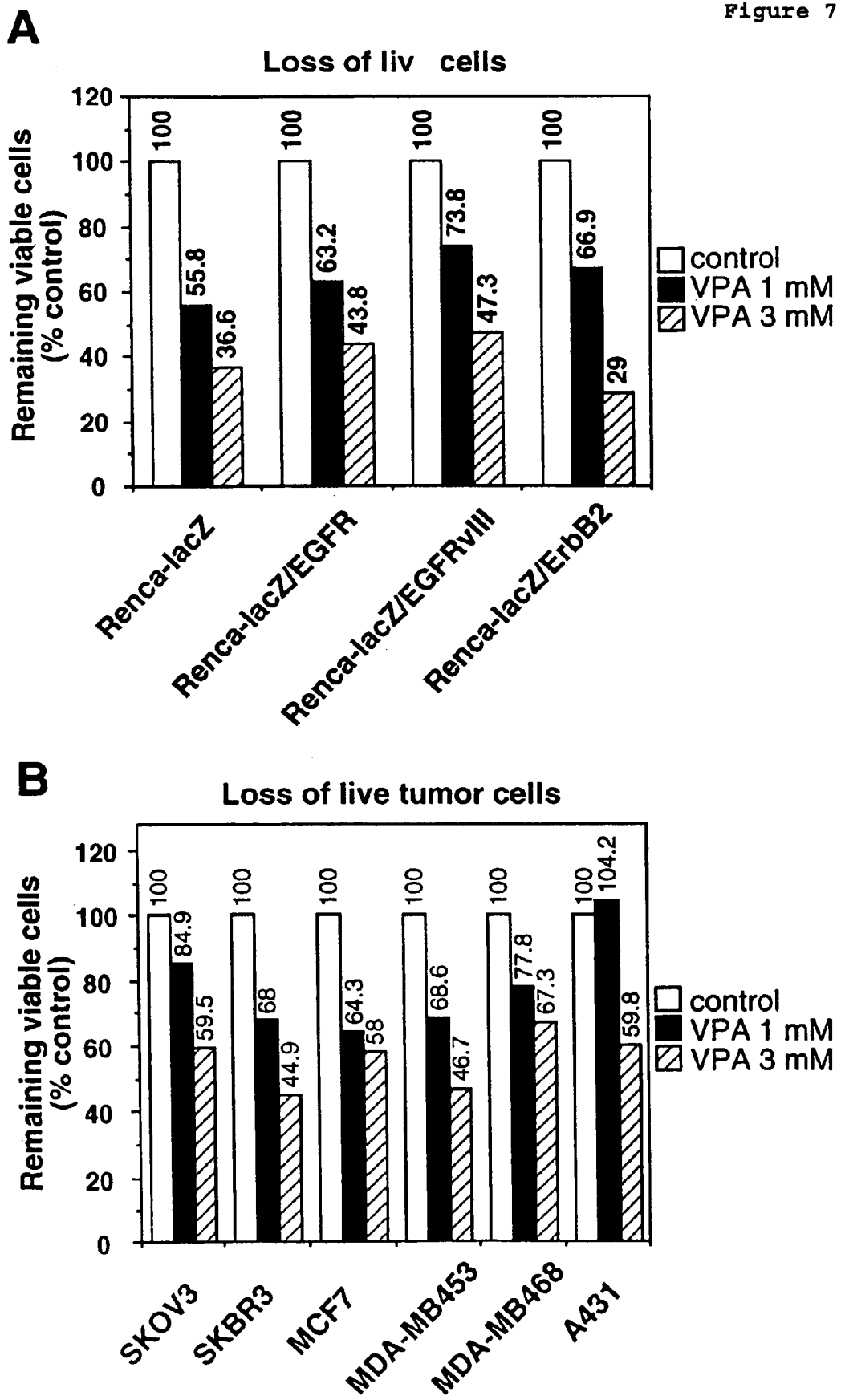
FIG. 7 shows the loss of viable cells upon treatment with valproic acid. Renca-lacZ, Renca-lacZ/EGFR, Renca-lacZ/EGFRvIII and Renca-lacZ/ErbB2 renal carcinoma cells (A)

The results presented in FIG. 7 show that valproic acid reduces the viability of breast carcinoma cells, ovarian carcinoma cells, squamous cell carcinoma cells, renal carcinoma cells, and renal carcinoma cells expressing at high levels the ErbB2 or EGF receptor proto-oncogenes, or the oncogenically activated EGF receptor variant EGFRvIII, in a concentration dependent manner. These results demonstrate that valproic acid potently reduces the number and/or viability of a wide variety of tumor cells derived from solid tumors of epithelial origin. The loss of viability could indicate a reduction in cell number upon induction of cellular differentiation and/or induction of cell death. The observation of changes of cellular morphology suggest that cellular differentiation is at least responsible for a part of the effect. This induction of differentiation and/or induction of cell death suggest that valproic acid and derivatives thereof could be used for the therapy of such tumors.

EXAMPLE 8

Reduction in Cellular Biomass After Treatment of Human Cancer Cell Cultures with Valproic Acid (See FIG. 8).

VPA induces differentiation and/or cell death in a series of human cancer cells and reduces the total cellular biomass of human cancer cell cultures. The reduction in biomass could indicate cell loss due to cell death and/or differentiation associated cell cycle arrest. Quantitative parameters, e.g. the loss of biomass, was determined in 30 human cancer cell lines (FIG. 8 e) and twelve examples of dose-response curves are shown, e.g. BT-549 breast cancer cells (1), estrogen dependent ZR-75 breast cancer cells (2), DMS-114 small cell lung cancer cells (3), NCl—H226 non-small cell lung cancer cells (4), SK-MEL-28 skin cancer cells (5), OVCAR-3 ovarian cancer cells (6), HUP-T3 pancreatic cancer cells (7), DU-145 prostate cancer cells (8), DETROIT-562 head and neck cancer cells, LS-174 colon cancer cells (10), A-172 brain cancer cells (11) and HL-60 leukemia cells (12) (FIGS. 8a-d). All cells were evaluated for morphological signs of cell death and/or differentiation. All cultures contained an increased number of dying cells at the highest tested VPA concentration and in some cultures such as SW-1116 colon cancer cells (FIG. 8 e) most cells were dying already at 1 mM VPA during the experiment. PC-3 (FIG. 8 e) and DU-145 (FIG. 8 c) cells change their normal round morphology to a long fibroblast-like shape. Also U87MG (FIG. 8 e) cells increase in length and develop spider-like filamentous extensions.

Cells in panels 1 to 9 (FIGS. 8a-c) were seeded in 96 well culture dishes at densities between 3000 and 8000 per well. After recovery of 24 hours cells were cultured for 48 hours in the absence or presence of the indicated concentrations of VPA. Cultures were fixed with TCA by layering 50 µl of cold 50% TCA on top of the growth medium in each well to produce a final TCA concentration of 10%. After 1 hour of incubation at 4° C. the cells were washed five times with tap water and air dried. Fixed cells were stained for 30 minutes with 0,4% (wt/vol) Sulforhodamine B dissolved in 1% acetic acid and washed four times with 1% acetic acid to remove unbound dye. After air drying bound dye was solubilized with 10 mM unbuffered Tris base (pH 10,5) for 5 minutes on a gyratory shaker. Optical densities were read on a Titertek Multiskan Plus plate reader at a single wavelength of 550 nm. Six test wells for each dose-response were set in parallel with 12 control wells per cell line. A measure of the cell population density at time 0 ($T_0$; the time at which the drug was added) was also made from 12 extra reference wells of cells fixed with TCA just prior to drug addition to the test plates. Background OD of complete medium with 5% FBS fixed and stained as described above was also determined in 12 separate wells.

From the unprocessed OD data the background OD measurements (i.e. OD of complete medium plus stain and OD of cells at $T_0$) were subtracted thus giving the reduction of total cellular biomass of the cells.

Cells in panels 10 to 12 (FIG. 8d) were cultured 36 to 50 hours as indicated in the absence or presence of the indicated concentrations of VPA in 96 well dishes. 37 kBq of $^3$H-thymidine were added for additional 12 hours of culture. Incorporation of $^3$H-thymidine into DNA was determined by automatic cell harvesting and liquid scintillation counting.

The graphs in FIGS. 8a-d show means±S.D. from sixfold determinations.

In addition cancer cells of further organ origins have been treated with valproic acid in the same way as described for experiments presented in FIGS. 8a-c. FIG. 8e summarizes the reduction of total cellular biomass of various human cancer cells by treatment with 1 mM VPA. This reduction could indicate differentiation associated cell cycle arrest and/or induction of cell death. Cells were VPA treated for 48 hours. The inhibition was calculated from six response tests performed in parallel and reductions of cellular biomass are given in percent of untreated cells with standard deviations.

The invention claimed is:

1. A method of treating cancer, comprising administering to a subject in need of such treatment, an agent capable of inhibiting histone deacetylase, selected from the group consisting of valproic acid, S-4-yn valproic acid, and 2-ethylhexanoic acid or a pharmaceutically acceptable salt; or a prodrug or pharmaceutically active metabolite, or a pharmaceutically acceptable salt of a prodrug or metabolite thereof.

2. The method of claim 1, wherein the cancer is colon or colorectal cancer.

3. The method of claim 1, wherein the cancer is skin cancer.

4. The method of claim 1, wherein the cancer is estrogen receptor-dependent and independent breast cancer.

5. The method of claim 1, wherein the cancer is ovarian cancer.

6. The method of claim 1, wherein the cancer is prostate cancer.

7. The method of claim 1, wherein the cancer is renal cancer.

8. The method of claim 1, wherein the cancer is pancreatic cancer.

9. The method of claim 1, wherein the cancer is head and neck cancer.

10. The method of claim 1, wherein the cancer is small cell and non-small cell lung carcinoma.

11. The method of claim 1, wherein the cancer is leukemia.

* * * * *